US00PP27034P3

(12) United States Plant Patent
Bagdasarian

(10) Patent No.: US PP27,034 P3
(45) Date of Patent: Aug. 9, 2016

(54) STRAWBERRY PLANT NAMED 'SCARLET'

(50) Latin Name: *Fragaria×ananassa*
Varietal Denomination: Scarlet

(71) Applicant: Jimmy Haig Bagdasarian, Santa Cruz, CA (US)

(72) Inventor: Jimmy Haig Bagdasarian, Santa Cruz, CA (US)

(73) Assignees: Jimmy H. Bagdasarian, Santa Cruz, CA (US); Lassen Canyon Nursery, Inc., Redding, CA (US)

( * ) Notice: Subject to any disclaimer, the term of this patent is extended or adjusted under 35 U.S.C. 154(b) by 178 days.

(21) Appl. No.: 14/120,950

(22) Filed: Jul. 14, 2014

(65) Prior Publication Data

US 2016/0014943 P1 Jan. 14, 2016

(51) Int. Cl.
*A01H 5/08* (2006.01)

(52) U.S. Cl.
USPC ..... Plt./209

(58) Field of Classification Search
USPC ..... Plt./209, 208
CPC ..... A01H 5/0893
See application file for complete search history.

*Primary Examiner* — Kent L Bell
(74) *Attorney, Agent, or Firm* — Catherine Ashley Straight

(57) ABSTRACT

A new and distinct variety of strawberry plant named 'Scarlet'. This new short day strawberry variety is partially remontant and is characterized by vigorous plants which produce very firm, long conical fruit having an attractive shape and large size, with a sweet strawberry flavor, and a very desirable lighter orange red exterior color.

7 Drawing Sheets

Latin name of the genus and species of the plant claimed: *Fragaria×ananassa.*

Variety denomination: 'Scarlet'.

BACKGROUND OF THE INVENTION

1. Field of Invention

The present invention relates to a new and distinct variety of strawberry named 'Scarlet'. This new short day strawberry variety is the result of a controlled cross in an ongoing breeding program made by the inventor, Jimmy Bagdasarian, in 2008. The variety is botanically known as *Fragaria×ananassa.*

The primary market for the 'Scarlet' variety is for the fresh market sales of the fruit. 'Scarlet' produces conical berries with few creases, which are large size and very firm.

2. Description of Relevant Prior Art

The controlled cross, conducted in the ongoing breeding program, which resulted in the 'Scarlet' variety, was between a strawberry variety designated '2F72', a male, and a strawberry variety designated '16F29', a female. The male parent, '2F72', is an unreleased proprietary variety having the following plant characteristics: strong short day variety; compact growth habit; medium vigor; leaves have medium glossiness with some blistering, and are slightly lighter in color than that of the female parent; somewhat irregular shaped fruit has a good flavor, and is very firm. The variety denomination of '16F29', the female parent, is 'Sweet Ann' (patented, U.S. Plant Pat. No. 22,472). The plant characteristics of 'Sweet Ann' are: day-neutral; globose with open plant density; strong vigor; leaves have medium glossiness with weak or absent blistering; with large size, conical fruit having a glossy medium red exterior and interior color.

The aforementioned controlled cross was carried out in a breeding program at Santa Cruz, Calif., USA. Pollen taken from a male '2F72' plant pollinated a '16F29' female plant. The flowers were covered so that no other pollen could contaminate the procedure.

Strawberries developed, were later harvested and the seeds resulting from this cross were extracted and germinated in a greenhouse at Redding, Calif., USA. The resulting seedlings were transplanted to Shastina, Calif. in 2009, grown for an additional period of time and allowed to propagate asexually. Plants were then harvested and planted in breeding plots in early to mid-October in: Oxnard, Calif. (Ventura County); and Watsonville, Calif. (Monterey County). The selection of the new variety was first made in Watsonville, Calif. This selection was designated '17J34' in 2010. The new variety was later named 'Scarlet'.

The new variety was further propagated asexually by stolons in breeding plots in: Macdoel, Calif. (Siskiyou County); and Manteca, Calif. (San Joaquin County).

The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, Calif.

The propagules of 'Scarlet' ('17J34') are identical to the original plant in all distinguishing characteristics; accordingly, the propagation has demonstrated that the traits disclosed herein remain fixed and true to type through successive generations of asexual reproduction.

SUMMARY OF THE INVENTION

Scarlet is a short day variety exhibiting the following combination of characteristics, which have been observed repeatedly, and which distinguish this strawberry plant as a new and distinct variety:

1. The variety produces large sized fruit;
2. The fruit is long conic, with few creases;
3. The fruit has a light to medium orange red exterior and a light red interior;
4. The fruit is sweet tasting, with excellent flavor;
5. The fruit is firm with superior retention of quality, appearance, and texture;
6. The plants of the variety are characterized by medium high vigor, with a large root system, and a semi-upright growth pattern; and,
7. The variety is partially remontant.

The fruit produced by the 'Scarlet' plant variety is larger than that of its male parent '2F72'. 'Scarlet' produces fruit which is large and sweet, but slightly smaller than its female parent 'Sweet Ann'. However, the fruit of 'Scarlet' is firmer than the fruit of 'Sweet Ann'.

The fruit of 'Scarlet' demonstrates other characteristics and qualities that are desired by fresh market strawberry sales companies. The lighter, medium orange red color is preferred by many shippers of fresh strawberries, as the deeper colored berries are more likely to be viewed as overripe by buyers than the lighter colored berries. In addition, 'Scarlet' plants have been grown in experimental plots with the fruit harvested and held in refrigeration; the fruit of 'Scarlet' retained its firmness, color, gloss, and quality even after seven (7) days holding time.

The plant vigor of 'Scarlet' is medium high with a large root system which provides an advantage over lower vigor varieties which require high fertility inputs to achieve similar vigor levels.

BRIEF DESCRIPTION OF THE DRAWING

The accompanying color photographs, identified as FIGS. 1 through 7, show the appearance of typical specimens of the new strawberry variety, initially designated '17J34', and now named 'Scarlet'. These Figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Scarlet' were taken in July of 2012.

DETAILED BOTANICAL DESCRIPTION OF THE PLANT

Figure 1:
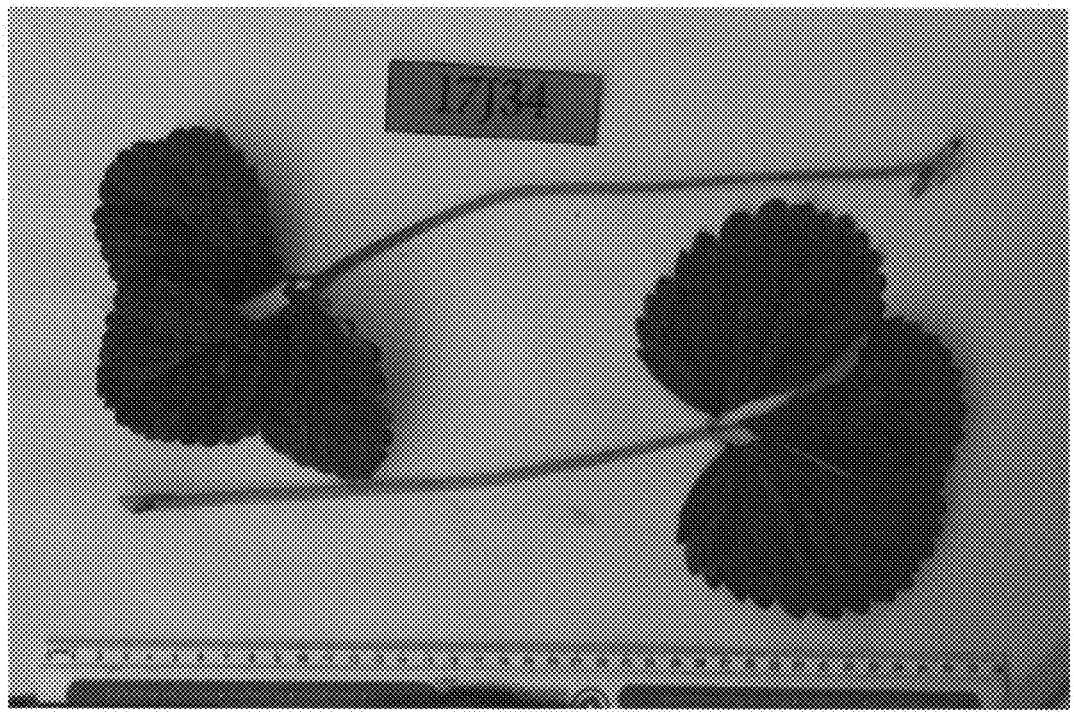
FIG. 1 shows typical leaf and petiole structures of 'Scarlet' at mid-season.
Figure 2:
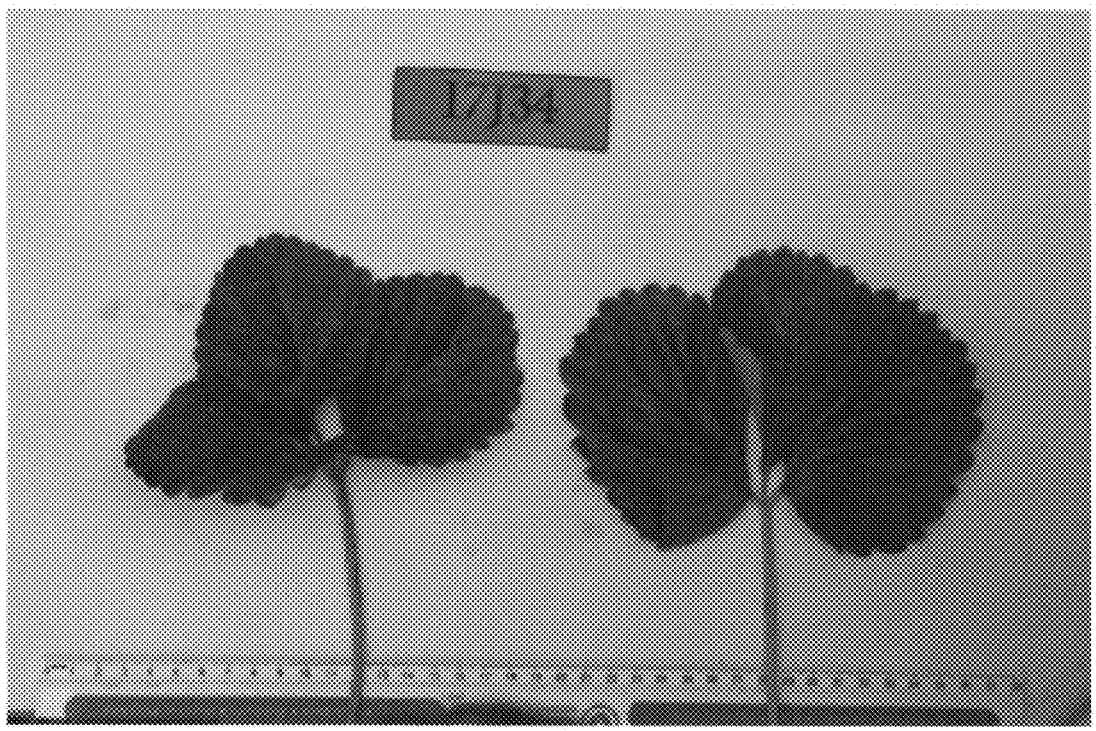
FIG. 2 shows typical leaf structure.
Figure 3:
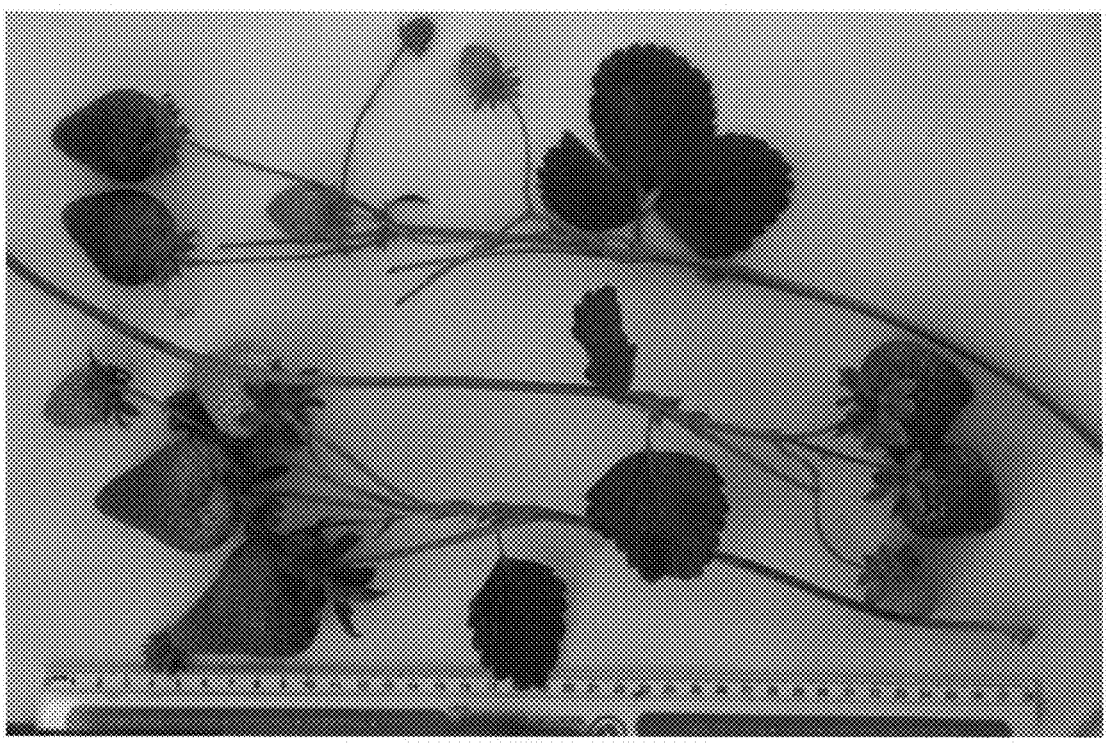
FIG. 3 shows a selection of typical mid-season fruit.
Figure 4:
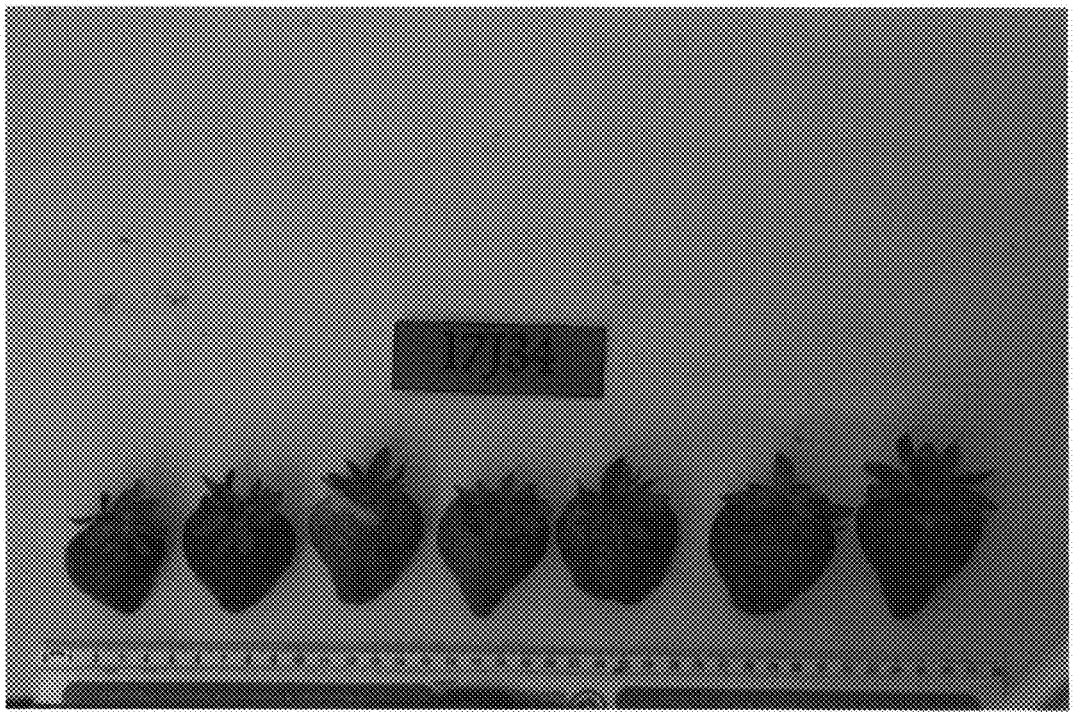
FIG. 4 shows typical fruit shape and calyx position over the berry of 'Scarlet'.
Figure 5:
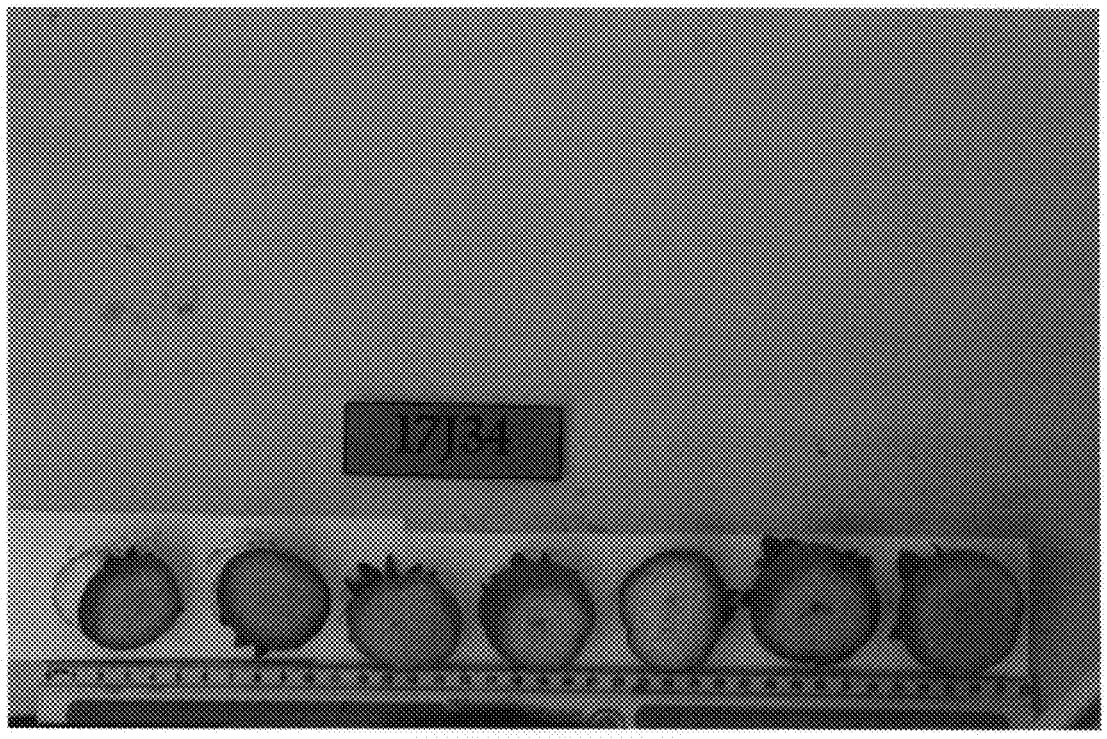
FIG. 5 shows a transverse cross-section of typical fruit internal coloration and core size.
Figure 6:
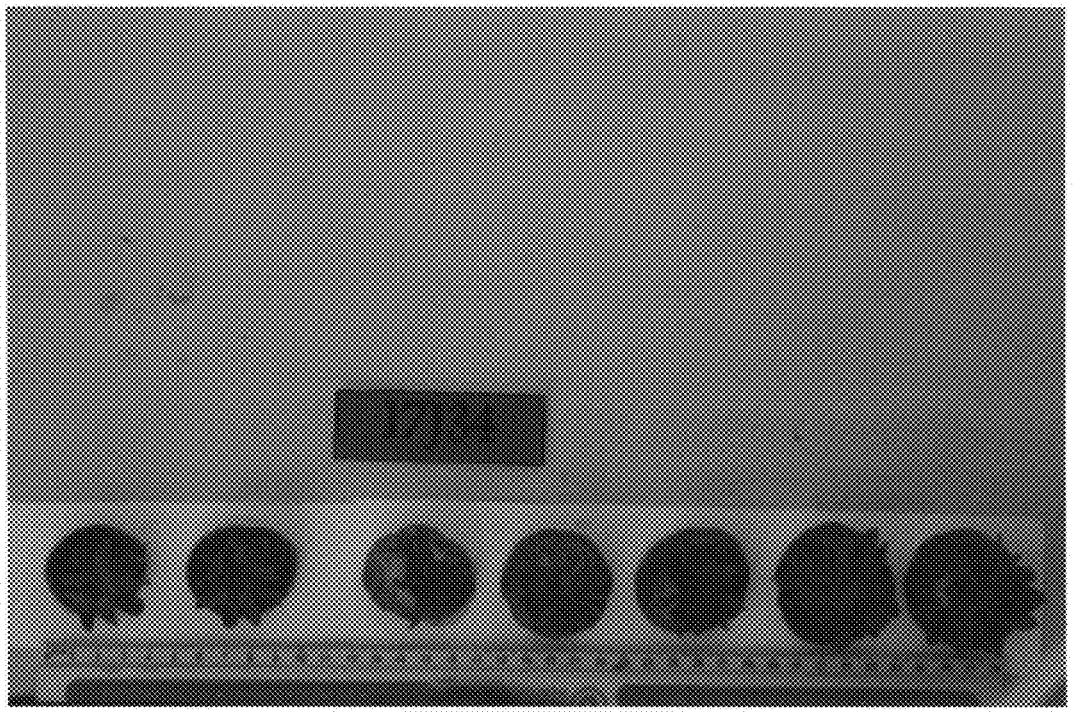
FIG. 6 shows calyx shape and relationship to fruit at mid-season.
Figure 7:
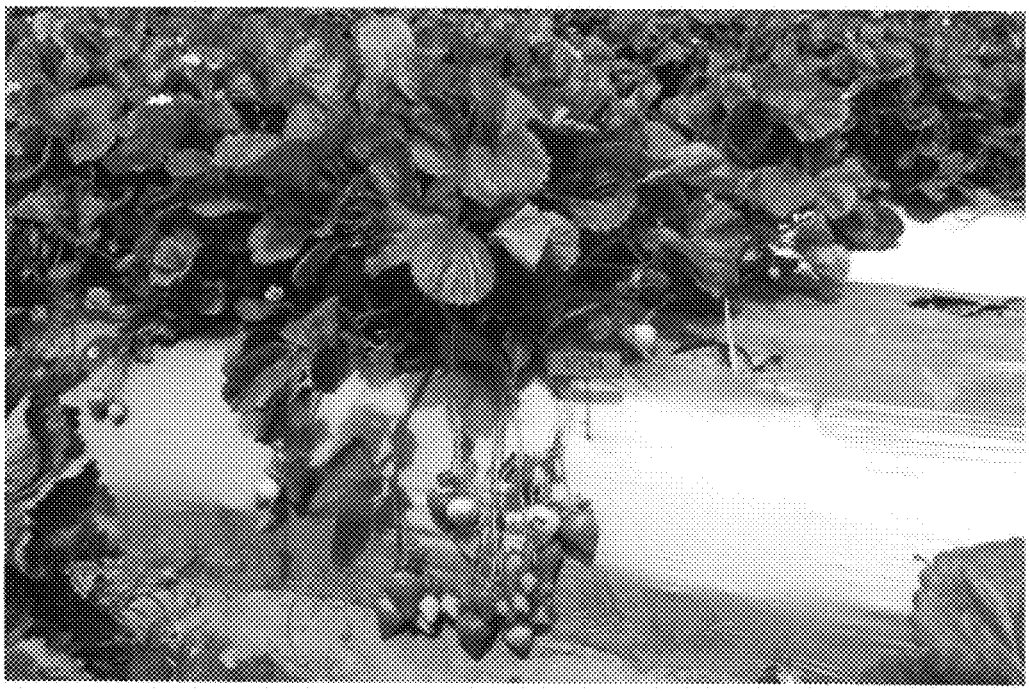
FIG. 7 shows typical fruiting plants in a field.

'Scarlet' is a new and distinct variety of strawberry, genus and species *Fragaria×ananassa*. It is the result of a cross between its male parent, '2F72', an unreleased proprietary variety, and 'Sweet Ann', U.S. Plant Pat. No. 22,472, its female parent. '2F72' is a strong short-day variety with partially remontant tendencies and 'Sweet Ann' is a day-neutral variety. 'Scarlet' is a short-day variety that is partially remontant. Mother plants have been observed blooming in production fields, but bloom only once in a high elevation nursery, consistent with a short-day variety. The plants of the new variety have a semi-upright growth habit, with medium high vigor and a large root system. 'Scarlet' exhibits several characteristics which are improvements over one or both of its parent varieties, and/or other known cultivars. The characteristics of 'Scarlet' were observed in plants aged four to eight months from planting. These characteristics and comparisons with other cultivars are discussed following. The fruiting pattern of 'Scarlet' is similar to that of 'Sweet Ann'. While the fruit size of 'Scarlet' is large, it is slightly smaller than the large fruit produced by 'Sweet Ann.' The fruit produced by 'Scarlet' is not as uniform, however, as that produced by 'Sweet Ann'. The slightly smaller size of fruit of 'Scarlet' does provide an advantage when grown in Northern California production areas where early risk of rain damage is high.

The fruit produced by '2F72' is irregular in shape with creasing down the sides. 'Scarlet' produces fruit with some creasing, but which is long conical like the female parent, 'Sweet Ann'. The fruit of 'Scarlet' ripens more evenly from the tip to the shoulders of the berry, resulting in a more uniform red color over the whole fruit. In contrast, the shoulders of the fruit of 'Sweet Ann' are the last portion to ripen. The fruit of 'Scarlet' is also firmer than the fruit 'Sweet Ann'. The fruit of 'Scarlet' holds very well in storage with less visible fruit bruising than observed with the fruit of many other varieties.

The data set forth for 'Scarlet' in Tables 1, 2, and 3 respecting the new variety was collected in August 2012 from plants grown at the test plot, in Prunedale, Monterey County, Calif. Color terminology where noted herein for 'Scarlet' and 'Sweet Ann' is in accordance with the Panton Color Formula Guide GP 1201.

In Table 1, the observed characteristics of 'Scarlet' are set forth.

TABLE 1

Detailed Description of Characteristics of 'Scarlet'

| | |
|---|---|
| SPECIFICATION: | |
| Genus/Species | *FragariaxAnanassa*. |
| Market name | Strawberry. |
| PARENTS: | |
| Male | Proprietary variety '2F72' (unpatented). |
| Female | 'Sweet Ann' (U.S. Plant Pat. No.22,472). |
| PLANT: | |
| Type | Short Day. |
| Growth habit | Semi-upright. |
| Foliage density | Dense. |
| Vigor | Medium high. |
| Height | Average: 33.5 cm; range: 29 cm to 38 cm. |
| Width | Average: 41.8 cm; range: 37 cm to 51 cm. |
| Crowns | Multiple crowns produced early after planting. |
| Disease tolerance | Test plants, grown in plots in areas with disease pressure, have shown excellent tolerance. In early- observations of-plants grown in a coastal California area, plants have exhibited excellent tolerance to *Fusarium oxysporum* (*Fusarium* wilt) as compared to 'Monterey' cultivar plants grown in,the same area. |
| LEAF: | |
| Width | Average: 19.1cm; range: 15 cm to 23.5 cm. |
| Color | Adaxial Surface: green 364 C.<br>Abaxial Surface: green 364 U. |

TABLE 1-continued

| Detailed Description of Characteristics of 'Scarlet' | |
|---|---|
| Pubescence | Medium density. |
| Inter-vein blistering | Low. |
| Glossiness | Medium-high. |
| Variegation | None. |
| TERMINAL LEAFLET: | |
| Length | Average: 9.96 cm. |
| Width | Average: 7.35 cm. |
| Ratio length to width | 1.36. |
| Margin | Serrate to obtuse. |
| Leaf shape | Orbicular. |
| Base shape | Acute to obtuse. |
| Cross-section shape | Concave. |
| PETIOLE: | |
| Pubescence | Medium to low density; direction: almost perpendicular. |
| Petiole color | Green 380 U. |
| Petiole length | Average: 23.25 cm. |
| Petiole diameter | Average: 4.44 mm. |
| STIPULE: | |
| Stipule anthocyanin coloration | Present, but mild. |
| Length | Average: 31.1 mm; range 22.2 to 35.4 mm. |
| Width | Average: 15.9 mm range 8.6 to 26.9 mm. |
| STOLON: | |
| Number produced. | Average: 16.8; range: 14 to 22. |
| Stolon anthocyanin | Present; mediwn intensity. |
| Pubescence | Medium high; up-wards direction. |
| Diameter | Average 4.0 mm; range: 3.5 mm to 4.4 mm. |
| INFLORESCENCE: | |
| Flowering time | Moderately early. |
| Position | Primary bract at or below. foliage with bloom above foliage. |
| Number of blooms | Average: 5; range: 3 to 7. |
| Length | Fruiting clusters mid-season: average 37.65 cm; range: 33 cm to 44.5 cm. |
| Flower | Average diameter: 34.27 mm;. range: 27.1 mm to 39.9 mm. |
| Petal arrangement | Overlapping. |
| Petal | Average number per flower: 6; range: 5 to 7. |
| Petal Length | Average: 13.34 mm; range: -10.9 mm to 16.8 mm. |
| Petal Width | Average: 13.04 mm; range: 10.9 mm to 15.11 mm. |
| Ratio length to width | 1.02. |
| Petal Color | Upper side: white, 11-4201 TPX. |
| Calyx | Size in relation to corolla: approximately equal. |
| Calyx color | Adaxial Surface: green 364 U. Abaxial Surface: green 370 U. |
| Stamens | Average number: 26.6; range 23 to 33. |
| Pedicel | Attitude of hairs is upwards. |
| FRUIT: | |
| Bearing | Partially remontant. |
| Shape | Long conical. |
| Length | Average: 5.26 cm; range: 4.0 cm to 7.0 cm. |
| Width | Average: 4.41 cm; range: 3.5 cm to 5.5 cm. |
| Ratio length to width | 1.20. |
| Size | Average grams per berry: 39.92 g. |
| Achenes | Approximately level with the fruit surface. |
| Glossiness | Strong. |
| External color | Orange red 179 C. |
| Internal color | Flesh, excluding core: red 178 C. |
| Evenness of external color | To the top of berry. |
| Width of band at top devoid of achenes | Small. |
| Fruit center | Little to some hollowness. |
| Firmness | Very firm. |
| Yield | Average grams per plant: 1,483 g. |

In Tables 2 and 3, the characteristics of 'Scarlet' are compared with the varieties 'Sweet Ann' (U.S. Plant Pat. No. 22,472) and 'Albion' (U.S. Plant Pat. No. 16,228). In Table 4, comparison is made between 'Scarlet' and several commercially grown cultivars. Color terminology where noted herein respecting all cultivars except 'Albion' is in accordance with the Panton Color Formula Guide. Color terminology respecting 'Albion' is in reference to the Munsell color system.

PLANTS AND FOLIAGE

The form and structure of the plants of 'Scarlet' are semi-upright with dense foliage. In comparison, 'Sweet Ann' plants are erect and open. The 'Scarlet' variety is slightly shorter than those of 'Sweet Ann'. The plants of 'Scarlet', like those of its parent 'Sweet Ann', are vigorous and are large in comparison to many other commercial cultivars grown in fresh strawberry production fields in California. In Table 2, comparative data for foliar characteristics are presented for 'Scarlet' and for two comparison cultivars, 'Sweet Ann' and 'Albion'

TABLE 2

Foliar Characteristics of 'Scarlet' Compared to 'Sweet Ann' and 'Albion'

| Foliar Characteristic | | Cultivar 'Scarlet' | 'Sweet Ann' | 'Albion' |
|---|---|---|---|---|
| Plant height (mm) | Average | 335 | 380 | 252 |
| | Range | 290-380 | 290-480 | 210-270 |
| Plant spread (mm) | Average | 418 | 420 | 341 |
| | Range | 370-510 | 330-510 | 304-394 |
| Leaf width (mm) | Average | 191 | 165 | 135 |
| | Range | 150-235 | 130-195 | 105-170 |
| Mid-tier leaflet length (mm) | Average | 100 | 88 | 73 |
| | Range | 95-130 | 72-105 | 50-95 |
| Mid-tier leaflet width (mm) | Average | 74 | 67 | 68 |
| | Range | 70-91 | 52-88 | 50-95 |
| Petiole length (mm) | Average | 233 | 220 | 105 |
| | Range | 190-280 | 150-280 | 70-130 |
| Petiole diameter (mm) | Average | 4.44 | 3.74 | 4.1 |
| | Range | 3.60-4.90 | 3.01-4.29 | 3.7-4.6 |
| Number leaflets per leaf | | 3 | 3 | 3 |
| Leaf convexity | | Concave | Slight concave | Some flat, most slight concave |
| Shape leaflet base | | Acute to obtuse | Obtuse | Obtuse |
| Leaf pubescence | | Medium density | Medium density | Light-moderate |
| Petiole pubescence | | Medium to low density | Medium-density | Heavy density |
| Direction | | Nearly Perpendicular | Perpen-dicular | Perpen-dicular |
| Stipule length (mm) | Average | 31.1 | Not available | 23.3 |
| | Range | 22.2-35.4 | | 14-34 |
| Stipule anthocyanin coloration | | Weak yes | Weak yes | Yes |
| Leaf margins | | Serrate to obtuse | Commonly crenate | Semi-pointed |
| Leaf color adaxial surface | | 364 C. | 364 U | 5GY 5/6 |
| Leaf color abaxial surface | | 364 U | 370 U | 5GY 4/4 |
| Petiole color | | 380 U | 383 U | 5GY 7/10 |
| Leaf surface blistering | | Low | Very weak | Medium |
| Leaf surface glossiness | | High | Medium | Low |

FLOWERING AND FRUIT

'Scarlet' is a short-day variety that is partially remontant. The primary flowers of 'Scarlet' are larger than those of 'Sweet Ann' and those of 'Albion'. The flowers of 'Scarlet' exhibit five to seven petals per bloom, similar to 'Sweet Ann' and 'Albion' which also exhibit variation, with flowers ranging from five to six for 'Sweet Ann' and five to eight petals per bloom for 'Albion'. In 'Scarlet', the calyx is similar to 'Sweet Ann'.

The exterior color of the fruit of 'Scarlet' tends toward orange red and is slightly lighter than that of 'Sweet Ann' and lighter than the deeper colored 'Albion' fruit. The interior color of the fruit of 'Scarlet' is also lighter than that of 'Sweet Ann' and of 'Albion' fruit. The fruit of 'Scarlet' has excellent culinary qualities, including: desirable shape and size, lighter red color than 'Albion', and a sweet strawberry flavor.

In Table 3, comparative data for flower and fruit characteristics for 'Scarlet', 'Sweet Ann' and 'Albion' are set forth.

TABLE 3

Flower and Fruit Characteristics of 'Scarlet' Compared to 'Sweet Ann' and 'Albion'

| Characteristic | Cultivar 'Scarlet' | 'Sweet Ann' | 'Albion' |
|---|---|---|---|
| Petal number | 5-7 | 5-6 | 5-8 |
| Petal length (mm): Average | 13.34 | 11.21 | 12.7 |
| Petal length (mm): Range | 10.9-16.8 | 9.2-13.13 | 11-15 |
| Petal width (mm): Average | 13.04 | 11.05 | 12.6 |
| Petal width (mm): Range | 10.9-15.11 | 9.0-13.10 | 11-14.0 |
| Position of flower (relative to foliage) | most exposed | most exposed, some even | most exposed, some even |
| Pedicel length (mm): Average | 377 | 330 | 113 |
| Pedicel length (mm): Range | 330-445 | 240-420 | 83-190 |
| Sepal color: Adaxial | 364 U | 364 U | 7.5GY 4/4 |
| Sepal color: Abaxial | 370 U | 370 U | 7.5GY 4/4 |
| Corolla diameter (mm): Average | 34-37 | 30.34 | 27 |
| Corolla diameter (mm): Range | 27.1-39.9 | 27.03-32.94 | 25-30 |
| Fruit color: External | 179 C. | 185 C. | 5R 3/7 |
| Fruit color: Internal | 178 C. | 1788 C. | 7.5R 3/6 |

The leaf and fruit color of 'Scarlet' is readily distinguished from that of several other commercially grown strawberry varieties. Table 4 shows the visually observed characteristics of the leaf and fruit colors of 'Scarlet' as compared to the leaf and fruit color characteristics of 'Sweet Ann', 'Chandler', 'Camarosa', 'Albion', and 'Catalina'.

TABLE 4

Comparison of Leaf and Fruit Colors of 'Scarlet' to Other Cultivars

| Cultivar | Color Adaxial Leaf | Color Abaxial Leaf | Color External Fruit | Color Internal Fruit |
|---|---|---|---|---|
| 'Scarlet' | 364 C. | 364 U | 179 C. | 178 C. |
| 'Sweet Ann' | 364 U | 370 U | 185 C. | 1788 C. |
| 'Chandler' | 343 C. | 339 U | 186 C. | 179 C. |
| 'Camarosa' | 349 C. | 348 U | 193 C. | 185 C. |
| 'Albion' | 5GY 3/2 | 5GY 5/6 | 5R 3/7 | 7.5R 3/6 |
| 'Catalina' | 343 C. | 349 U | 193 C. | 185 C. |

Leaf samples from 'Scarlet', along with two advanced proprietary (unpatented) selections from the breeding program: '42J4' and '33K46', were submitted to a lab for allelic fingerprint comparison to the control variety, "Camarosa," and the over two hundred other varieties of strawberry in its data base. The allelic fingerprint analysis establishes that 'Scarlet' is distinct and unique compared to the lab's large database of allelic fingerprints. Table 5 below sets forth the test results:

TABLE 5

Allelic Fingerprint Analysis

| Cultivar | M1 | M2 | M3 |
|---|---|---|---|
| '42.14' | 202, 204, 206, 229 | 188, 216, 232 | 235, 241, 245, 269 |
| 'Scarlet' '17J34' | 204, 206, 214, 229 | 173, 190, 232 | 231, 243, 245, 265, 269 |
| '33K46' | 206, 224, 229 | 188, 190, 216, 232 | 235, 241, 245, 265 |
| 'Camarosa' | 214, 222, 224, 229 | 188, 190, 216, 232 | 247, 265 |

PERFORMANCE

Performance with respect to fruit size, yield, and appearance for 'Scarlet' was assessed by making comparisons with its female parent, 'Sweet Ann', and two advanced proprietary (unpatented) selections from the breeding program: '42J4' and '33K46'. All plants for these trials were initially grown at a high elevation nursery in Macdoel, Siskiyou County, Calif. The plants were dug on October 16$^{th}$, and planted after eleven days of supplemental storage on Oct. 27, 2012. The varieties were planted and evaluated at Elkhorn, Monterey County, Calif. The yield data for the comparisons are based upon 18,000 plants per acre, converted to yield in grams per plant. The fruit for these trials was harvested from April through August, 2013.

The average fruit size of 39.92 grams per berry for 'Scarlet' is larger than that of 'Albion' (33.0 g/berry), but smaller than the fruit of its female parent 'Sweet Ann'. Fruit from 'Scarlet' has more uniformity regarding size as compared to 'Sweet Ann'. The fruit of 'Scarlet' fruit retains its attractive appearance, even very ripe, as compared to other cultivars, maintaining its desirable characteristics during shipment of the fruit to market. The fruit from the trials was rated based upon commercial appearance using a scale wherein a numerical score of "5" represents the best appearance score. 'Scarlet' rated very good, with a score of "3.75," as compared to both 'Sweet Ann' and 'Albion', each of which have a commercial appearance rating of "4.0." Table 6 shows the performance of 'Scarlet' compared to 'Sweet Ann', and the proprietary unpatented varieties designated '42J4' and '33K46'.

TABLE 6

Comparison of Performance of 'Scarlet' to 'Sweet Ann' '42J4' and '33K46'

| Cultivar | Yield grams/plant | Size grams/berry | Appearance Rating 5 =Best |
|---|---|---|---|
| 'Scarlet' | 1,483 | 39.92 | 3.75 |
| 'Sweet Ann' | 1,738 | 47.5 | 4.0 |
| '42J4' | 1,057 | 33.25 | 4.5 |
| '33K46' | 919 | 29.42 | 3.75 |

I claim:

1. A new and distinct strawberry plant named 'Scarlet' as herein described and illustrated by the characterizations set forth above.

* * * * *